United States Patent [19]

Sebag et al.

[11] Patent Number: 4,523,921
[45] Date of Patent: Jun. 18, 1985

[54] SURFACE-ACTIVE POLYSILOXANES

[75] Inventors: Henri Sebag, Paris; Guy Vanlerberghe, Claye-Souilly, both of France

[73] Assignee: L'Oreal, Paris, France

[21] Appl. No.: 644,618

[22] Filed: Aug. 27, 1984

Related U.S. Application Data

[60] Continuation of Ser. No. 345,097, Feb. 2, 1982, abandoned, which is a division of Ser. No. 98,329, Nov. 27, 1979, Pat. No. 4,342,742.

[30] Foreign Application Priority Data

Dec. 5, 1978 [FR] France .................. 78 34268

[51] Int. Cl.³ .................. A61K 7/13; A61K 7/06
[52] U.S. Cl. .................. 8/405; 8/406; 8/407; 424/70
[58] Field of Search .......... 8/405, 406, 407; 424/70

[56] References Cited

U.S. PATENT DOCUMENTS

| | | | |
|---|---|---|---|
| 3,624,120 | 11/1971 | Yetter | 556/418 |
| 3,957,970 | 5/1976 | Korkis | 424/70 |
| 3,964,500 | 6/1976 | Drakoff | 424/70 |
| 4,005,117 | 1/1977 | Heckert et al. | 556/418 |
| 4,005,118 | 1/1977 | Heckert et al. | 556/418 |
| 4,005,119 | 1/1977 | Heckert et al. | 556/418 |
| 4,093,642 | 6/1978 | Schilling | 556/413 |
| 4,243,657 | 1/1981 | Okmura et al. | 424/70 |
| 4,374,825 | 5/1983 | Bolich, Jr. et al. | 424/70 |

FOREIGN PATENT DOCUMENTS 1508055  4/1978  United Kingdom .

Primary Examiner—Albert T. Meyers
Assistant Examiner—John M. Kilcoyne
Attorney, Agent, or Firm—Cushman, Darby & Cushman

[57] ABSTRACT

Surface-active polysiloxanes are disclosed having the formula:

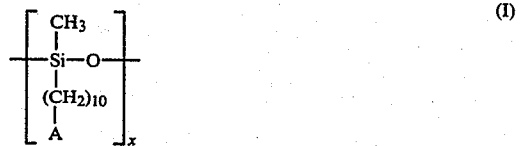

(I)

in which x denotes an integer from 3 to 10 and A denotes a cationic, anionic, zwitterionic or nonionic hydrophilic unit which contains one or more of the same or different groups which are amine, amine oxide, ammonium, ammonioalkylcarboxylate, ammonioalkylsulphonate, amide, sulphonamide, ether, thioether, sulphoxide, hydroxyl, ester or acid groups. These polysiloxanes are particularly useful for use in cosmetic and pharmaceutical compositions, especially compositions for the hair.

7 Claims, No Drawings

SURFACE-ACTIVE POLYSILOXANES

This is a continuation of application Ser. No. 345,097 filed Feb. 2, 1982 now abandoned, which is a divisional of Ser. No. 98,329 filed Nov. 27, 1979 now U.S. Pat. No. 4,342,742.

The invention relates to surface-active, cyclic and/or linear polysiloxanes, processes for their preparation and compositions in which they are present.

The surface-active polysiloxanes of this invention possess remarkable properties, in particular an amphiphilic character, that is to say an affinity for both water and organic media, which imparts a high interfacial activity thereto.

They also differ from conventional surface-active agents which comprise a single lipophilic chain per molecule.

As is well known, when the latter are dissolved in water, they show, beyond a concentration threshold referred to as the "critical micellar concentration", a group of properties which are very advantageous for a large number of different purposes. In particular, at concentrations which are at least equal to this threshold, they solubilize organic substances, such as liposoluble dyestuffs and hydrocarbons, in water.

The compounds according to the invention possess solubilizing properties at very low concentrations; they are frequently well below the critical micellar concentration of surface-active agents which comprise a lipophilic chain of comparable length. This constitutes a significant advantage for certain uses of surface-active agents, such as in pharmaceutical or cosmetic compositions where it is advantageous to reduce to a minimum the amount of surface-active compound used, so as not to interfere with the active principle in these compositions.

Moreover, the compounds of the invention are less aggressive towards the skin and mucous membranes, in particular the mucous membranes of the eye, and/or they denature proteins less than surface-active agents comprising a single lipophilic chain per molecule and comparable functional groups.

The surface-active polysiloxanes of this invention can be represented by the general formula:

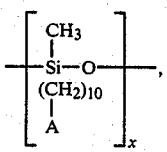

(I)

in which A denotes a hydrophilic unit which is connected to the chain via the decamethylene group $-(CH_2)_{10}-$ constituting the lipophilic component, and x denotes an integer from 3 to 10 and preferably from 3 to 6.

The polysiloxanes of the formula (I) are generally in cyclic form. However, the invention also includes linear polysiloxanes of the formula (I). The cyclic and/or linear polysiloxanes can be in the form or single compounds or in the form of a mixture of compounds.

The hydrophilic unit A can be cationic, zwitterionic, anionic or non-ionic. It can comprise one or more (identical or different) groups which are amine, amine oxide, ammonium, ammonioalkylcarboxylate, ammonioalkylsulphonate, amide, sulphonamide, ether, thioether, sulphoxide, hydroxyl, ester or acid groups.

The hydrophilic unit A is typically one of the following groups:

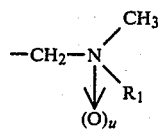

(a)

in which $R_1$ denotes $CH_3$ or $-(CH_2-CH_2-O)_n H$, where u denotes 0 or 1 and n denotes any number from 1 to 10;

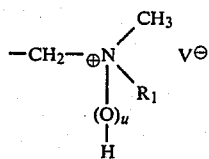

(b)

in which $V^-$ denotes the anion of an organic or mineral acid, preferably a chloride, bromide, sulphate, phosphate, acetate glycolate, lactate, tartrate, methanesulphonate or para-toluenesulphonate anion, $R_1$ is as defined under (a) and u denotes 0 or 1;

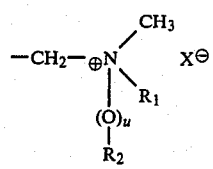

(c)

in which $R_2$ denotes a methyl, hydroxyethyl or dihydroxypropyl radical, $X^-$ denotes an anion, preferably a chloride, bromide, iodide, methylsulphate, mesylate or tosylate anion, and $R_1$ and u are as defined under (a);

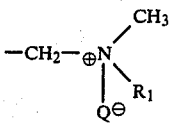

(d)

in which $Q^-$ denotes one of the groups: $-CH_2COO^-$, $-CH_2-CH_2COO^-$ and $-CH_2$13 $CH_2-CH_2-SO_3^-$, and $R_1$ is as defined under (a);

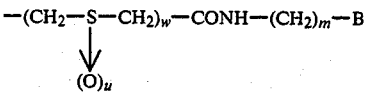

(e)

in which m denotes 2 or 3, w denotes 0 or 1, u denotes 0 or 1 and B denotes the group:

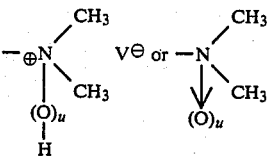

Furthermore, if w denotes zero, B can also denote the group:

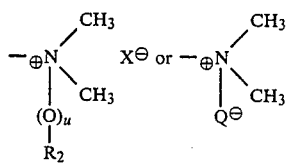

In these groups: u denotes 0 or 1, $Q^\ominus$ is as defined under (d), $R_2$ and $X^\ominus$ are as defined under (c) and $V^\ominus$ is as defined under (b);

$$—CH_2—O—SO_2NH—(CH_2)_m—B \qquad (f)$$

in which m denotes 2 or 3 and B is as defined under (e) when w=0;

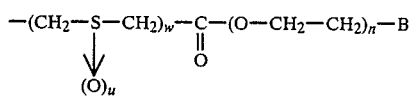

in which n is as defined under (a), w denotes 0 or 1 and u and B are as defined under (e);

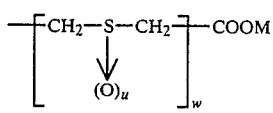

in which M denotes a hydrogen atom, an ammonium group or an alkali metal, such as lithium, sodium or potassium, and u and w, which are identical or different, denote 0 or 1;

$$—CH_2—O—SO_3M \qquad (i)$$

in which M is as defined under (h);

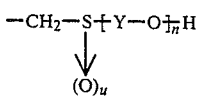

in which Y denotes the ethylene or hydroxypropylene radical, u denotes 0 or 1 and n denotes any number from 1 to 10; and

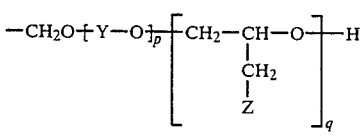

in which p and q, which are identical or different, denote 0 or any positive number up to 10, it being impossible for p and q simultaneously to denote 0, Y is as defined under (j) and Z denotes one of the following groups:

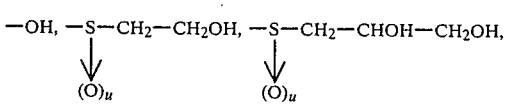

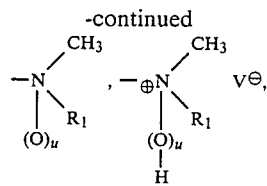

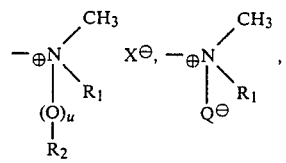

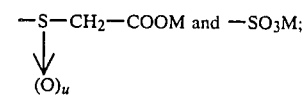

$$—OSO_3M \text{ or } —OCO—CH_2—SO_3M.$$

In these groups: u denotes 0 or 1, $R_1$ is as defined under (a), $V^-$ is as defined under (b), $R_2$ and $X^-$ are as defined under (c), $Q^\ominus$ is as defined under (d) and M is as defined under (h).

The distribution of the units:

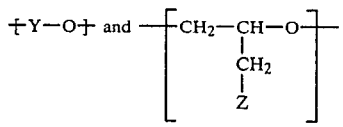

in (k) is most generally a block distribution, as indicated by the formula (k). However, particularly when Y denotes the hydroxypropylene group, the distribution can also be random.

The compounds of the formula (I) can be prepared in several stages which comprise (1) the reaction of the acetic acid ester of undecylenyl alcohol or the methyl or ethyl ester of undecylenic acid with methyldichlorosilane and (2) controlled hydrolysis, and polymerization with the removal of water, followed by (3) one or more reactions intended to introduce the desired hydrophilic unit A.

The reaction of an ester indicated above with methyldichlorosilane can be carried out in an autoclave, at a temperature of say, 110° C.-130° C., advantageously in the presence of hexachloroplatinic acid, typically as a solution in methanol.

This reaction can be represented schematically in the following way:

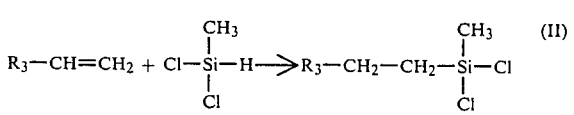

in which $R_3$ denotes $CH_3—C(=O)—O—(CH_2)_9—$,

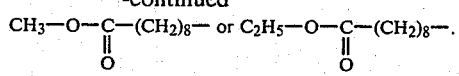

As a result of controlled hydrolysis, which is advantageously carried out in the presence of sodium hydroxide or potassium hydroxide, the chlorine atoms are replaced by hydroxyl groups.

The resulting product is dehydrated and polymerizes to form a cyclic or linear compound. The compounds formed are generally cyclic.

The hydrolysis and polymerization reactions are generally carried out in a mixture of water and an inert solvent, such as tetrahydrofurane or dioxane, at a temperature from 0° to 80° C., advantageously from 0° to 40° C. and preferably from 0° to 10° C.

Depending on whether the acetic acid ester of undecylenyl alcohol or the methyl or ethyl ester of undecylenic acid is used as the starting material, the intermediate obtained has the formula (III) or (IV):

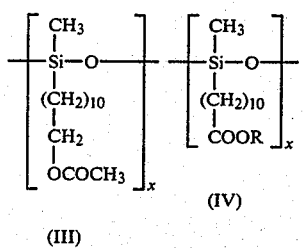

in which x denotes an integer from 3 to 10, preferably from 3 to 6, and R denotes $CH_3$ or $C_2H_5$.

Saponification of the compounds of the formulae (III) and (IV) leads to the compounds of the formulae (IIIa) and (IVa) respectively:

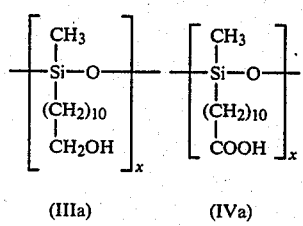

in which x has the meaning indicated above.

The present invention also provides the intermediates and the mixtures of intermediates, of the formula:

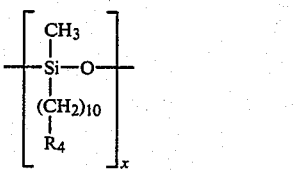

in which $R_4$ denotes $-CH_2OCOCH_3$, $-CH_2OH$, $-COOCH_3$ or $-COOC_2H_5$ and x denotes an integer from 3 to 10 and preferably from 3 to 6 which are produced before or after saponification.

The invention also provides a process for the preparation of surface-active polysiloxanes, which comprises (1) the reaction of the acetic acid ester of undecylenyl alcohol or the methyl or ethyl ester of undecylenic acid with methyldichlorosilane under the conditions specified above, (2) the replacement of the chlorine atoms by hydroxyl groups as described above, and (3) the replacement of the groups $-CH_2-OCOCH_3$, $-COOCH_3$ or $-COOC_2H_5$ formed, by hydrophilic groups (a), (b), (c), (d), (e), (f), (g), (h), (i), (j) and (k) defined above.

The compounds of the type I(a), i.e. those of formula I in which A denotes the group (a), can be prepared by reacting dimethylamine or methylethanolamine either with the chlorinated or brominated derivative of the intermediate of the formula (IIIa) (which derivative can be obtained by reacting the compound of the formula (IIIa) with thionyl chloride or hydrobromic acid respectively) or with the mesylate or tosylate of the intermediate of the formula (IIIa) (which can be obtained by mesylation or tosylation respectively).

In other words, the compounds of the type I(a) can be prepared by reacting dimethylamine or methylethanolamine with the intermediate of the formula (VI)

in which x denotes an integer from 3 to 10, preferably from 3 to 6, and $R_5$ denotes $-CH_2Cl$, $-CH_2Br$, $-CH_2-O-SO_2-CH_3$ or $-CH-O-SO_2-C_6H_4-CH_3$.

The condensation of the amine can be carried out at atmospheric pressure or in an autoclave, suitably at a temperature from 20° to 160° C., optionally in the presence of an alkaline compound, such as sodium methylate. If methylethanolamine is used, the compound obtained can be oxyethyleneated if desired. The amine group can be converted into the amine oxide by oxidation, for example with hydrogen peroxide or a peracid.

The compounds of the type I(b), i.e. those of formula (I) in which A denotes the group (b), can be obtained from the compounds I(a) by salification with a mineral or organic acid and advantageously with one of the following: hydrochloric acid, hydrobromic acid, sulphuric acid, phosphoric acid, acetic acid, glycolic acid, lactic acid, tartaric acid, methanesulphonic acid and para-toluenesulphonic acid.

The compounds of the type I(c), i.e. those of formula (I) in which A denotes the group (c), can be prepared by alkylating the compounds I(a) with an alkylating agent, such as methyl chloride, bromide, iodide, sulphate, mesylate or tosylate, glycol chlorohydrin or glycerol chlorohydrin.

The compounds of the type I(c) in which $X^-$ denotes a mesylate (methanesulphonate) or tosylate (p-toluenesulphonate) anion can be obtained by reacting the mesylate or tosylate of the intermediate of the formula (IIIa) with an amine of the formula

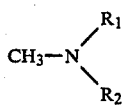

in which $R_1$ denotes $CH_3$ or $-(CH_2-CH_2-O)_{\overline{n}}H$, n denoting any number from 1 to 10, and $R_2$ denotes a methyl, hydroxyethyl or dihydroxypropyl radical, suitably at a temperature of 20° to 120° C.

The compounds of the type I(d), corresponding to the formula (I) in which A denotes the group (d), can be prepared by alkylating the compounds I(a) with sodium chloroacetate or chloropropionate, methyl or ethyl chloroacetate or chloropropionate or propane-sultone.

The compounds of the type I(e), corresponding to the formula (I) in which A denotes the group (e), can be prepared, if w denotes zero, by condensing the intermediate of the formula IV

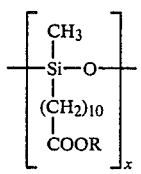
(IV)

in which R denotes $CH_3$ or $C_2H_5$ and x denotes an integer from 3 to 10 and preferably from 3 to 6, with an appropriate primary/tertiary diamine, for example dimethylaminoethylamine or dimethylaminopropylamine.

If w denotes 1, the compounds of the type I(e) can be obtained by condensing an appropriate primary/tertiary diamine with the intermediate of the formula (VII)

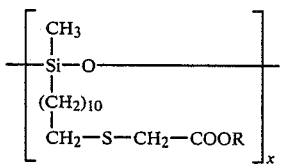
(VII)

in which R denotes $CH_3$ or $C_2H_5$ and x has the above meaning, which intermediate can be obtained by reacting methyl or ethyl thioglycolate with the intermediate of the formula:

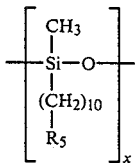
(VI)

in which x has the above meaning and $R_5$ denotes —$CH_2Cl$, —$CH_2Br$, —$CH_2$—O—$SO_2$—$CH_3$ or —$CH_2$—O—$SO_2$—$C_6H_4$—$CH_3$.

The intermediate of the formula (VI) can be prepared by reacting the intermediate of the formula (IIIa) with thionyl chloride, hydrobromic acid, mesyl chloride or tosyl chloride respectively, depending on whether $R_5$ denotes —$CH_2Cl$, —$CH_2Br$, —$CH_2$—O—$SO_2CH_3$ or —$CH_2$—O—$SO_2$—$C_6H_4$—$CH_3$.

The condensation of the primary/tertiary diamine is suitably carried out at a temperature of 20° to 160° C.

The amine group and the sulphur atom (when w=1) can be oxidized to the amine oxide and the sulphoxide, respectively, for example with hydrogen peroxide or a peracid at a temperature of 10° to 100° C.

Moreover, the tertiary amine or amine oxide groups of the aminoamides thus obtained can then be salified with a mineral or organic acid as indicated for the compounds of the type I(b), and, if u=0, they can be alkylated with alkylating agents such as those indicated for the compounds of the type I(c) and I(d).

The compounds of the type I(f), corresponding to the formula (I) in which A denotes the group (f), can be obtained by reacting sulphuryl chloride, $SO_2Cl_2$, with the intermediate of the formula (IIIa) and then condensing the resulting products with an appropriate primary/tertiary diamine at a temperature of 0° to 120° C.

The tertiary amine group can be oxidized to the amine oxide, and the tertiary amine group or the resulting amine oxide group can be salified and/or alkylated in the same way as the corresponding groups of the compounds of the type I(e).

The compounds of the type I(g), corresponding to the formula (I) in which A denotes the group (g), w denoting zero, can be obtained from the product resulting from the condensation, with the removal of alcohol or water, of the intermediate of the formula (IV) or (IVa) with the oxyethyleneated dimethylamine of the formula:

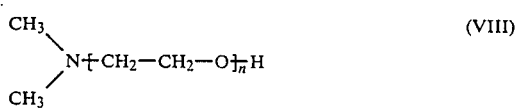
(VIII)

in which n denotes any number from 1 to 10.

The compounds of the type I(g) in which w denotes 1 can be obtained from the product resulting from the condensation of the oxyethyleneated dimethylamine of the formula (VIII) with a compound of the formula (VII) at a temperature of, for example, 20° to 160° C.

In the same way as for the compounds of the type I(e), the amine groups and the sulphur atom (when w=1) can be oxidized to amine oxide and sulphoxide groups respectively, and, moreover, the tertiary amine or amine oxide groups of the aminoamides thus obtained can then be salified and/or alkylated under the conditions and with the reagents indicated for the compounds of the type I(e).

The compounds of the type I(h), corresponding to the formula (I) in which A denotes the group (h), can be prepared, if w denotes zero, by the saponification of the intermediate (IV)

(IV)

in which R denotes $CH_3$ or $C_2H_5$, with ammonia or an alkali metal hydroxide, optionally followed by acidification when M denotes hydrogen.

If w denotes 1, the compounds of the type I(h) can be prepared by the saponification of the intermediate of the formula (VII) with an alkali metal hydroxide or ammonia, optionally followed by acidification, it being possible for the sulphur atom present to be oxidized to the sulphoxide with, say, hydrogen peroxide or a peracid.

The compounds of the type I(i), corresponding to the formula (I) in which A denotes the group (i), can be prepared by reaction of the intermediate of the formula (IIIa) with chlorosulphonic acid and neutralization, if appropriate, with ammonia or an alkali metal hydroxide.

These reactions can be carried out without a solvent or in the presence of a solvent, such as chloroform, benzene, toluene or ether, suitably at a temperature from 0° to 80° C.

The compounds of the type I(j), corresponding to the formula (I) in which A denotes the group (j), can be obtained by reacting mercaptoethanol or mercaptoglycerol with the intermediate of the formula (VI). These reactions are generally carried out in a solvent (preferably ethanol, propanol, isopropanol, t-butanol, butan-1-ol, glycols or glycol monoethers, optionally with water), in the presence of sodium methylate or ethylate or potassium methylate or ethylate, or sodium hydroxide or potassium hydroxide, at a temperature from 60° to 160° C. 1 to 9 mols of ethylene oxide and/or of glycidol can be added, at 120° C.–180° C., to the compounds thus obtained, in the presence of an alkaline catalyst such as sodium methylate, ethylate or hydroxide or potassium methylate, ethylate or hydroxide, in order to give water-soluble compounds. If both ethylene oxide and glycidol are added, the reactions are generally carried out in two successive steps.

The reactions can be carried out with or without a solvent; suitable solvents which can be used include: water, isopropanol, tert.-butanol, methyl ethyl ketone and methyl isobutyl ketone.

The compounds of the type I(k), corresponding to the formula I in which A denotes the group (k), can be obtained, in one or more steps, by means of polyaddition reactions of reagents having an epoxide group with the intermediate of the formula (IIIa) or with a polysiloxane of the type I(j), that is to say a compound of the formula (I) in which A denotes the group (j), in the presence of an acid catalyst, such as boron trifluoride or tin tetrachloride, or in the presence of a basic catalyst, such as sodium methylate or ethylate or potassium methylate or ethylate; a basic catalyst should not be used for the polyaddition of epihalogenohydrins.

Epoxides which can be used include ethylene oxide, tert.-butyl glycidyl ether (TBGE) and/or an epihalogenohydrin, such as epichlorohydrin or epibromohydrin and mixtures thereof.

The polyaddition reactions are generally sequential operations but, in the case where TGBE and an epihalogenohydrin are used, it is also possible to add the two reagents simultaneously or as a mixture.

The tert.-butoxy protective groups can be replaced by hydroxyl groups by heating at, say, 50°–120° C. in the presence of a strong acid, such as a sulphocarboxylic acid.

The halogen atoms in the oligomers obtained by reaction with an epihalogenohydrin can be replaced by a hydroxyl, thiohydroxyethyl, thiodihydroxypropyl, thioglycolate, amine, ammonium, ammonioacetate, ammoniopropionate, ammoniopropanesulphonate or sulphonate group.

The replacement of the halogen atoms by hydroxyl groups can be effected by reaction with an alkali metal salt of a carboxylic acid, preferably with sodium acetate or potassium acetate, suitably at a temperature of 150° to 260° C., in a suitable solvent which is advantageously a glycol or glycol derivative; the acetic acid ester formed is then decomposed by saponification, using sodium hydroxide or potassium hydroxide, by hydrolysis, or by alcoholysis using a lower alcohol, preferably methanol or ethanol, in the presence of a basic catalyst which is preferably sodium methylate or ethylate or potassium methylate or ethylate.

The hydroxyl groups can then be replaced by sulphate or sulphoacetate groups by esterification with chlorosulphonic acid or with sulphoacetic acid.

The replacement of the halogen atoms by thiohydroxyethyl, thiodihydroxypropyl or thioglycolate groups can be effected by reaction with thioethanol, thioglycerol or methyl or ethyl thioglycolate, at a temperature of, say, 20°–150° C., in the presence of an alkaline compond which is advantageously sodium hydroxide, methylate or ethylate or potassium hydroxide, methylate or ethylate, and optionally in the presence of a solvent.

The replacement of the halogen atoms by amine groups can be effected as for the compounds of the type I(a).

The amine groups and the sulphur atom present can be oxidized to amine oxide and sulphoxide groups using hydrogen peroxide or an organic peracid.

Moreover, the amine or amine oxide groups can be salified and/or alkylated, as indicated for the compounds I(b), I(c) and I(d), and converted into an ammonium group.

The replacement of the halogen atoms by the ammoniopropanesulphonate, ammonioacetate or ammoniopropionate group can be effected in two steps. In a first step, the halogen is replaced by an amine group, and, in a second step, the amine is alkylated either with an acid of the formula Hal—$CH_2$—$CH_2$—$CH_2$—$SO_3H$, in which Hal denotes chlorine or bromine, or with the sodium or potassium salt of this acid, or, preferably, with propanesultone to give the propanesulphonate group, or with chloroacetic or chloropropionic acid or methyl or ethyl chloroacetate or chloropropionate, in the presence of a basic compound, such as sodium methylate, ethylate or hydroxide or potassium methylate, ethylate or hydroxide, to give the ammonioacetate or ammoniopropionate groups, for example at a temperature of 20° to 150° C.

The replacement of the halogen atom by a sulphonate can be effected by heating in an autoclave with sodium sulphite in aqueous solution or in a mixture of water and a hydroxyl compound containing up to 6 carbon atoms, for example, an alcohol, glycol or alkoxyethanol.

In the last case, the reaction can be carried out directly with t-butoxy groups.

The compounds of the formula (I) which contain oxidizable nitrogen or sulphur atoms can be oxidized in accordance with a conventional process using hydrogen peroxide or peracids, such as peracetic acid or performic acid, generally at a temperature from 10° to 100° C., and converted into amine oxides or sulphoxides.

The surface-active polysiloxanes of the formula (I), according to the invention, are in the form of powders, pastes or oils, which are generally soluble or dispersible in water.

Amongst the water-insoluble compounds which can be solubilized by the surface-active polysiloxanes of the formula (I), there should be mentioned dyestuffs, perfumes and certain pharmaceutical products.

Apart from solubilizing these products, the surface-active polysiloxanes of the formula (I) can make it possible to solubilize or disperse inorganic or polar compounds in an organic medium or hydrophobic compounds in an aqueous medium.

The compounds of the invention can be used in various industries, in particular in the cosmetic and pharmaceutical industries and in the textile, dyeing and insecticide industries.

This invention also provides compositions containing at least one surface-active polysiloxane of the formula (I).

Amongst these compositions, there may be mentioned more particularly cosmetic and pharmaceutical compositions containing at least $0.5 \times 10^{-2}$ gram per liter (or $0.5 \times 10^{-3}\%$ by weight) of surface-active polysiloxane of the formula (I).

The cosmetic compositions include, in particular, compositions intended for the care of the skin, the nails and the hair.

The hair-care compositions are preferably aqueous compositions which can be used as such although they can also contain adjuvants conventionally used in compositions for the treatment of keratinic material.

The most interesting results of the compounds of this invention can be observed in the cosmetics field and, in particular, when they are used for the treatment of hair.

These cosmetic compositions can be in the form of, for example, an aqueous, alcoholic or aqueous alcoholic solution, a cream, a gel, an emulsion or a powder or provided as an aerosol in the presence of a propellant. The pH is generally from 2 to 11.

Suitable adjuvants which can be present in these compositions include non-ionic, anionic, cationic and amphoteric surface-active agents well-known in the art, animal, mineral, vegetable or synthetic oils and waxes, fatty alcohols, anionic, cationic, non-ionic and amphoteric resins conventionally used in cosmetics, emulsifiers, solar filters, organic solvents, thickeners, opacifiers, preservatives, sequestrants, anti-oxidants, perfumes, nacreous material, dyestuffs, pigments, pH modifiers, reducing agents, oxidizing agents, natural substances, protein derivatives, antiseborrheic agents, anti-dandruff agents, restructuring agents, active substances having an effect on the treatment, care or protection of the skin or hair.

These compositions are, in particular, used in the form of shampoos, rinsing lotions to be applied before or after shamooing, before or after dyeing or bleaching or before or after permanent waving, hair styling or restructuring lotions, treatment lotions such as antiseborrheic and anti-dandruff lotions, brushing lotions, hair lacquers, setting lotions and permanent waving compositions.

The cosmetic compositions for the hair are, in particular:

(a) treatment compositions or pre- or post-hair treatment compositions. The application of these compositions to the hair is optionally followed by rinsing after, say, one to thirty minutes.

These various treating compositions can contain a variety of adjuvants and, in particular, polyethylene glycols and their derivatives, anionic, cationic, amphoteric and non-ionic resins conventionally used in hair compositions, pH modifiers, protein derivatives such as optionally quaternized protein hydrolysates, natural substances such as plant extracts, fatty alcohols such as cetyl, stearyl, cetylstearyl and oleyl alcohols, these alcohols optionally being polyethoxylated or polyglycerolated, animal, vegetable, mineral or synthetic oils and waxes such as vaseline oil (liquid petrolatum), maize oil, wheatgerm oil, olive oil, soya oil, castor oil and avocado oil, these oils and waxes being optionally oxyethylenated, anti-seborrheic materials, anti-dandruff materials, re-structuring agents such as methylolated derivatives as well as other cosmetic adjuvants conventionally used in cosmetic compositions for the hair;

(b) shampoos which contain at least one anionic, non-ionic or amphoteric surface-active agent or mixtures thereof and a compound of formula (I) in an aqueous medium. These compositions can also contain various adjuvants conventionally used in such compositions such as cationic surface-active agents, dyestuffs in the case of dyeing shampoos, preservatives, thickeners, foam-stabilizers foam synergists, softening agents, sequestering agents, cosmetic resins, perfumes, protein derivatives, natural substances, and oils as well as other adjuvants used in shampoos. In these shampoos, the concentration of detergent is generally from 2 to 50 percent by weight. Amongst non-ionic detergents specific mention can be made of the condensation products of a mono-alcohol, α-diol, alkylphenol, amide or diglycolamide with glycerol, such as the non-ionic surface-active agents described in French Pat. Nos. 1,477,048, 2,091,516 and 2,328,763 as well as U.S. Pat. Nos. 3,578,719, 3,821,372, 3,928,224 and U.S. Ser. No. 735,216 and polyethoxylated or polyglycerolated alcohols, alkylphenols, or fatty acids having a linear chain of 8 to 18 carbon atoms and generally containing 2 to 30 mols of ethylene oxide, ethylene oxide/propylene oxide copolymers, condensates of ethylene or propylene oxide with fatty alcohols, polyethoxylated fatty amides, polyethoxylated fatty amines, ethanolamides, glycol esters of fatty acids, sorbitol esters of fatty acids and saccharose esters of fatty acids.

Suitable anionic surface-active agents which can be used, optionally combined with non-ionic surface-active agents, include, in particular, alkaline, ammonium, amine or amino-alcohol salts of the following compounds: alkyl sulphates, alkyl ether sulphates, alkyl amide sulphates and alkyl-amido ether sulphates, alkylaryl polyether sulphates, monoglycerido sulphates, alkyl sulphonates, alkyl-amido-sulphonates, alkyl aryl sulphonates, α-olefin sulphonates, alkyl-sulpho-succinates, alkyl ether sulphosuccinates, alkyl-amido-sulphosuccinates, alkyl sulphosuccinamates, alkyl-sulpho-acetates, alkyl polyglycerol carboxylates, alkylphosphates, alkyl ether phosphates, alkyl sarcosinates, alkyl polypeptidates, alkyl amidopolypeptidates, alkyl isethionates and alkyl taurates.

The alkyl radical in all these compounds generally has a linear chain of 12 to 20 carbon atoms. Other compounds include fatty acids such as oleic, ricinoleic, palmitic, stearic, copra oil, hydrogenated copra oil acids and the carboxylic acids of polyglycol ethers corresponding to the formula:

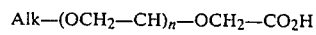

Alk—(OCH$_2$—CH)$_n$—OCH$_2$—CO$_2$H where Alk represents a linear chain having 12 to 18 carbon atoms and n is an integer from 5 to 15. Of course, other anionic detergents can be used.

Typical amphoteric surface-active agents which can be used include alkylamino betaine, mono- and di-propionates such as N-alkylbetaines, N-alkylsulphobetaines, N-alkylamidobetaines, cyclo imide derivatives such as alkylimidazolines and asparagine derivatives. The alkyl group in these surface-active agents is preferably one having from 1 to 22 carbon atoms.

Suitable foam stabilizers include fatty amides and, in particular, the mono- and di-ethanolamides of copra fatty acids, the mono- and di-ethanolamides of lauric and oleic acid, these generally being used in an amount of 1 to 10 percent, preferably 1 to 3 percent, by weight based on the weight of the composition.

Suitable thickeners include acrylic polymers and cellulose derivatives such as carboxymethylcellulose, hydroxypropylmethyl cellulose and hydroxyethylcellulose. These thickeners are generally present in an amount of 0.1 to 5 percent by weight;

(c) dyeing compositions for the hair and, in particular, oxidation dye compositions containing oxidation dye precursors such as those of the ortho or para type optionally with one or more couplers, in a basic medium, preferably having a pH from 8 to 11 and/or leuco derivatives of one or more indamines, indoanilines and indophenols as well as direct dyestuffs well known in the art, or dyeing compositions intended for direct or semipermanent dyeing which contain direct dyestuffs such as the nitrobenzene, azo or anthraquinone dyes as well as indamines, indoanilines and indophenols;

(d) bleaching compositions which can be provided in the form of a powder, solution, emulsion or gellable liquid as well as a cream containing at least one bleaching agent such as hydrogen peroxide or other peroxide or a solution of a persalt such as a persulphate, a perborate or percarbonate and at least one compound of formula (I). These compositions generally contain an alkaline agent such as ammonia.

These bleaching compositions can be applied in a conventional manner;

(e) permanent waving compositions or compositions for fixing the hair.

The formulation of the reducing and oxidizing (fixing) compositions is well known and is described in standard works on cosmetology such as "Problémes Capillaires", E. Sidi et C. Zviak, Paris 1966 (Gauthier-Villard). For permanent waving according to the present invention one of the two types of composition contains a compound of formula (I). The reducing compositions also contain a reducing agent, as well as one or more adjuvants which enable the composition to be in the form of, for example, a lotion, a powder to be dispersed in a liquid vehicle and optionally a compound of formula (I). Their pH is generally from 7 to 10.

The reducing agent is most frequently a mercaptan such as thioglycerol or thioglycolic acid or a derivative thereof.

The compositions according to this invention can also be applied to the skin and can be in one of the different forms mentioned above. The compositions confer on the skin a softness to the touch.

They generally contain as well as one or more compounds of formula (I) a variety of cosmetic adjuvants conventionally used for the skin and, in particular, perfumes, dyestuffs, pigments, preserving agents, sequestering agents, emulsifying agents, thickening agents and sun filters.

The compositions are, in particular, in the form of creams, lotions for the hands or face, anti-sun creams, coloring creams, make-up removing milks, shaving creams, oils or foaming liquids for the bath, deodorizing compositions, all of which can be prepared in a conventional manner.

This invention also provides a process for treating the hair, the skin or the nails, which comprises applying thereto a sufficient amount of a composition of the present invention.

The following Examples further illustrate the present invention; in these Examples x denotes an integer from 3 to 10.

EXAMPLE 1

Preparation of a mixture of intermediates, of the formula:

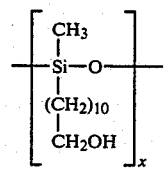

(IIIa)

169 g (0.8 mol) of the acetic acid ester of undecylenyl alcohol, 102 g (0.88 mol) of methyldichlorosilane and 0.5 ml of a 2% strength solution of hexachloroplatinic acid in methanol are introduced into a 1 liter autoclave. The mixture is heated for 5 hours at 120° C. The reaction mixture is filtered on a glass frit; the unreacted methyldichlorosilane is then distilled under reduced pressure and the dichloro derivative is then distilled at 150° C. under a pressure of 0.5 mm Hg. 750 ml of tetrahydrofurane and a solution of 56 g (1 mol) of potassium hydroxide in 200 ml of water are added.

The mixture is cooled in an ice bath to +5° C.; a solution of the dichloro derivative in 750 ml of tetrahydrofurane is then added at a temperature between 5° and 10° C. Duration of addition: 1 hour 40 minutes. After stirring for a further 30 minutes, the tetrahydrofurane is removed under reduced pressure and the organic phase is recovered by decantation, then dried over dry sodium sulphate and then purified by molecular distillation at a temperature of 285° C. under a pressure of $10^{-3}$ mm Hg. 95 g of the compound thus obtained are dissolved in 500 ml of 96° strength ethanol; 40 g of a sodium hydroxide solution containing 10 milliequivalents/g are then added under reflux. After heating for 1 hour 30 minutes, the alcohol is removed under reduced pressure. The residue is taken up in 100 ml of water and 200 ml of ether. The organic phase is separated off by decantation and dried over dry sodium sulphate. 78 g of product are thus obtained; this product is in the form of a wax which is characterized by gas phase chromatography and infra-red spectroscopy; it has a pour point of 52° C.

EXAMPLE 2

Preparation of a mixture of intermediates, of the formula:

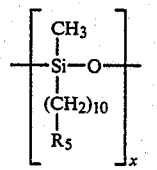

(VI)

in which $R_5$ denotes the group $CH_2Cl$.

9.2 g of the intermediate of the formula (IIIa), prepared in accordance with Example 1, are dissolved in 70 ml of benzene.

4 g (0.02 mol) of triethylamine are then added and a solution of 9.5 g (0.08 mol) of thionyl chloride in 40 ml of benzene is then added at ambient temperature in the course of 30 minutes.

After heating under reflux for 5 hours, the triethylamine hydrochloride is filtered off and rinsed twice with 10 ml of benzene.

The filtrate is evaporated to dryness under reduced pressure.

9.5 g of compound are thus obtained; this compound is in the form of a black oil.

Organic chlorine: 4.71 milliequivalents/g.

EXAMPLE 3

Preparation of a mixture of compounds, of the formula:

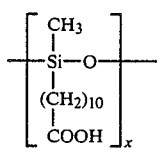
(IVa)

1st step: Preparation of the methyl ester:

A mixture of 99 g (0.5 mol) of methyl undecylenate, 63.5 g (0.55 mol) of methyldichlorosilane and 0.5 ml of a 2% strength solution of hexachloroplatinic acid in methanol is heated in an autoclave at 120° C. for 5 hours.

After filtration, the residual reactants are removed by distillation under reduced pressure and 98 g of the dichloro derivative are then distilled at a temperature of 155°–160° C. under a pressure of 2 mm Hg.

500 ml of tetrahydrofurane are added to a solution of 36 g of KOH in 130 ml of water; a solution of 98 g (0.32 mol) of the dichloro derivative in 500 ml of tetrahydrofurane is then added at a temperature of 5°–10° C. Duration of the reaction: 1 hour 30 minutes.

After removal of the tetrahydrofurane, the organic phase is separated off by decantation, dried over sodium sulphate and then purified by molecular distillation at a temperature of 285° C.

An oil is thus obtained which has a saponification number of 3.85 milliequivalents/g and which is characterised by gas phase chromatography and infra-red spectroscopy.

2nd step: Saponification of the ester:

52 g of the product thus obtained are dissolved in 200 ml of 96° strength ethanol, and 24 g of a 40% strength aqueous solution of sodium hydroxide and 70 ml of water are then added under reflux.

After heating for 30 minutes, the alcohol is removed under reduced pressure, the residue is taken up in 170 ml of water and the mixture is then acidified with 55 ml of 6N hydrochloric acid.

The desired acid is filtered off, washed with water and then dried.

A solid product is thus obtained which has a melting point of 40° C. and an acid number of 4 milliequivalents/g and is soluble in water in the presence of a base, such as sodium hydroxide or triethanolamine.

EXAMPLE 4

Preparation of a mixture of compounds, of the formula:

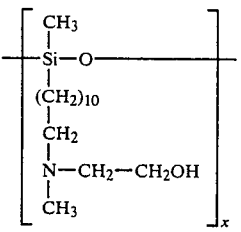

3.2 g (40 milliequivalents) of methylethanolamine are added to a solution, in 25 ml of toluene, of 4.5 g (20 milliequivalents of chlorine) of the intermediate chloro derivative of the formula (VI), prepared in accordance with Example 2. After heating under reflux for 10 hours, the reaction mixture is cooled and 4 g of a solution of sodium methylate in methanol, containing 5 milliequivalents/g, are then added at ambient temperature. After stirring for ½ hour, the sodium chloride formed is filtered off and the solvent is removed under reduced pressure.

A product is thus obtained which is in the form of an oil which is soluble in water in the presence of a mineral or organic acid.

Base number: 3.58 milliequivalents/g.

EXAMPLE 5

Preparation of a mixture of compounds, of the formula:

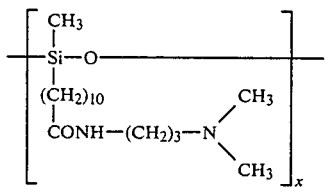

5.1 g (50 milliequivalents of primary amine groups) of N,N-dimethylaminopropylamine are added to 10 g (40 milliequivalents) of the methyl ester of the formula (IV), in which R denotes CH$_3$, obtained in accordance with the first step of Example 3.

After heating for 6 hours at 100° C. under a nitrogen atmosphere, the excess amine is distilled under reduced pressure.

The residual product is in the form of a brown oil which is soluble in water in the presence of a mineral or organic acid.

Base number: 2.7 milliequivalents/g.

Tertiary amine number: 2.5 milliequivalents/g.

EXAMPLE 6

Preparation of a mixture of compounds, of the formula:

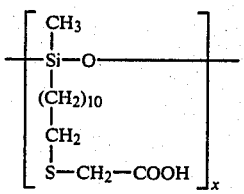

2.3 g (19.2 milliequivalents) of ethyl thioglycolate are added, at 50° C., to a solution, in 40 ml of isopropanol, of 3.85 g (19.2 milliequivalents) of the intermediate of the formula (VI) prepared in accordance with Example 2, and 4.8 g of a solution of sodium methylate in methanol, containing 4 milliequivalents/g, are then added dopwise. The reaction mixture is heated under reflux for 10 hours. After the sodium chloride formed has been filtered off, 20 ml of 96° strength ethanol, 5 ml of water and 1.55 g of an aqueous solution of sodium hydroxide, containing 10 milliequivalents/g, are added. After heating under reflux for 1 hour, the solvent is removed under reduce pressure, the residue is then taken up in 50 ml of water and the mixture is washed twice with 10 ml of chloroform.

The aqueous solution is acidified with 10 ml of 2N hydrochloric acid and then extracted with 3 times 10 ml of chloroform.

The organic phase is dried over sodium sulphate and then concentrated to dryness.

The resulting product is in the form of a wax which is soluble in water in the presence of a base, such as sodium hydroxide or triethanolamine.

Acid number: 2.9 milliequivalents/g.

EXAMPLE 7

Preparation of a mixture of compounds, of the formula:

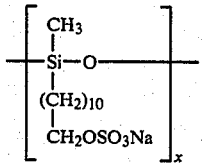

5.5 g (23.5 milliequivalents of hydroxyl groups) of the intermediate of the formula IIIa, prepared in accordance with Example 1, are dissolved in 10 ml of chloroform.

2.72 g (23.5 milliequivalents) of chlorosulphonic acid in 5 ml chloroform are then added, whilst keeping the temperature at 20°-25° C. After stirring for 30 minutes, the solvent is removed under reduced pressure and the residue is taken up in 25 ml of absolute ethanol; the acid is neutralized with 4.7 g of a solution of sodium methylate in methanol, containing 5 milliequivalents/g. The sodium salt is filtered off, rinsed with absolute ethanol and then dried.

A white solid, which dissolves in water giving a slight opalescence, is thus obtained.

| Elementary analysis: | C % | H % | S % |
|---|---|---|---|
| | 40.04 | 7.38 | 8.30 |
| | 40.21 | 7.04 | 8.44 |

EXAMPLE 8

Preparation of a mixture of compounds, of the formula:

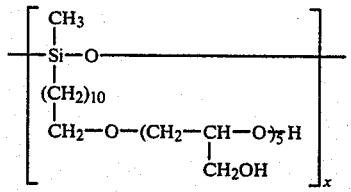

0.18 ml of born trifluoride/ether complex is added to 9.8 g of the compound of the formula IIIa, prepared in accordance with Example 1, and 25.9 g (200 milliequivalents) of tert.-butyl glycidyl ether are then added at 50° C.

After heating for 2 hours at 70° C., 0.35 g of sulphoacetic acid is added and the mixture is gradually heated to 90° C. in the course of 3 hours.

5 ml of water are added and the mixture is heated for 4 hours at 100°-105° C. After cooling, the reaction mixture is taken up in 300 ml of water and the catalyst is neutralized in the presence of 40 g of ion exchange resin (Amberlite MB 1).

The resin is then filtered off and rinsed twice with 50 ml of water.

After evaporation to dryness, a paste is obtained which dissolves in water to give an opalescence. Hydroxyl number: 8.6 milliequivalents/g.

EXAMPLE 9

Preparation of a mixture of compounds, of the formula:

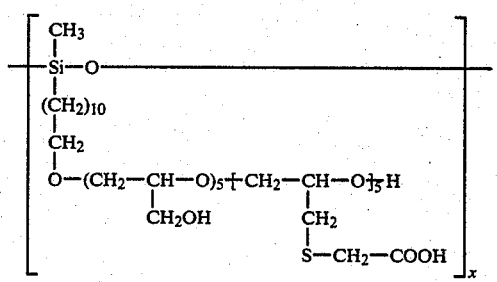

0.24 ml of boron trifluoride etherate is added to 8 g (35 milliequivalents) of the compound of the formula IIIa, prepared in accordance with Example 1, and a mixture of 22.7 g (175 milliequivalents) of tert.-butyl glycidyl ether and 16.3 g (175 milliequivalents) of epichlorohydrin is then added, at 70° C., in the course of 1½ hours.

After heating for 4 hours, 0.45 g of sulphoacetic acid is added and the mixture is heated for 3 hours at 90° C. After adding 2 ml of water, the mixture is heated for a further 1 hour 30 minutes at 105° C.

12 g (100 milliequivalents) of ethyl thioglycolate are added, at a temperature of 40° C., to a solution, in 50 ml of absolute ethanol, of 19.6 g (100 milliequivalents of chlorine) of the compound thus obtained, and 25 g (100 milliequivalents) of sodium methylate are then added dropwise. After heating under reflux for 2 hours, the sodium chloride is filtered off and the solvent is then removed under reduced pressure. The residue is taken up in 60 ml of 96° strength ethanol, and 9.3 g of a sodium hydroxide solution containing 10 milliequivalents/g are added thereto.

40 ml of water are added and the mixture is heated under reflux for 1 hour. 25 ml of 3N hydrochloric acid are then added. The product is salted out, washed 4 times with 30 ml of water and then dried. A brown wax is thus obtained which is soluble in water in the presence of a base, such as sodium hydroxide or triethanolamine.

Acid number: 3.4 milliequivalents/g.

EXAMPLE 10

The following dyeing composition was prepared:

| | |
|---|---|
| Triethanolamine salt of the compound of Example 3 | 1.2 g |
| 1,4-di(methylamino)-2-nitro benzene | 0.07 g |
| Water qs (sufficient quantity) | 100 g |

This solution was applied for 20 minutes to bleached hair. It provided, after rinsing, shampooing and rinsing, a pale pink cyclamen shade.

EXAMPLE 11

The following dyeing composition was prepared:

| | |
|---|---|
| Triethanolamine salt of the compound of Example 6 | 1 g |
| 4-N—(β-hydroxyethyl)amino-4-phenyl-azo-nitro-phenol | 0.08 g |
| Water qs | 100 g |

This solution was applied for 30 minutes to bleached hair; it provided after rinsing, shampooing and rinsing, a pink champagne shade.

EXAMPLE 12

A colored setting lotion was prepared as follows:

| | |
|---|---|
| Triethanolamine salt of the compound of Example 6 | 1 g |
| Vinylpyrrolidone/Vinyl acetate (60/40) copolymer | 2 g |
| Nitroparaphenylenediamine | 0.1 g |
| Water qs | 100 g |

Applied to bleached hair, this colored setting lotion conferred a salmon shade to the hair.

EXAMPLE 13

The following dyeing composition was prepared:

| | |
|---|---|
| Triethanolamine salt of the compound of Example 3 | 1.2 g |
| Paratoluylene diamine dihydrochloride | 0.24 g |
| Para aminophenol | 0.1 g |
| 2-methyl-5-[N—(β-hydroxyethyl) amino] phenol | 0.15 g |
| 1-methoxy 3-nitro-4-[N—(β-hydroxyethyl) amino] benzene | 0.2 g |
| Cetyl alcohol | 18 g |
| 20% ammonium lauryl sulphate | 12 g |
| Cetyl stearyl alcohol oxyethylenated with 13 moles of ethylene oxide | 3 g |
| Lauryl alcohol | 5 g |
| 22° Ammonia | 13 cm³ |
| Sodium salt of diethylene triamine pentacetic acid | 3 g |
| Water qs | 100 g |

At the time of use, an equal quantity of 6% hydrogen peroxide was added to the cream obtained, and the resulting mixture applied to bleached hair.

After 30 minutes, after rinsing, shampooing, rinsing and drying, the hair possessed a rosewood shade.

EXAMPLE 14

An anionic shampoo was prepared as follows:

| | |
|---|---|
| Triethanolamine salt of the compound of Example 3 | 1 g |
| Triethanolamine lauryl sulphate | 7 g |
| Lauryl diethanolamide | 1.5 g |
| Hydrochloric acid qs pH 7.5 | |
| Water qs | 100 g |

EXAMPLE 15

A non-ionic shampoo was prepared from the following:

| | |
|---|---|
| Compound of Example 7 | 0.8 g |
| Hydroxyalkylether of polyglycerol of the formula: R—CHOH—CH₂—O$\{$CH₂—CHOH—CH₂—O$\}_{3.5}$H in which R represents a mixture of alkyl radicals having 9 to 12 carbon atoms | 7 g |
| Diethanolamide of the fatty acids of copra | 3 g |
| Hydrochloric acid qs pH 7.3 | |
| Water qs | 100 g |

The shampoos of Examples 14 and 15 were applied to the head of hair previously wetted so as to emulsify all the dirt. The hair was rinsed and a second application made; a voluminous foam was obtained. After rinsing, the hair was soft and after winding on setting rollers, a good hold of the hair was observed.

We claim:

1. In a composition for dyeing hair comprising an aqueous or aqueous-alcoholic carrier, a hair dye and a surfactant, the improvement comprising, as said surfactant at least $0.5 \times 10^{-3}$ weight percent of at least one of a cyclic or linear polysiloxane, or a mixture thereof, having the formula

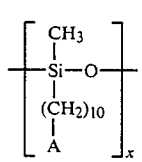

wherein x is an integer from 3 to 10, and

A is a cationic, anionic, zwitterionic or non-ionic hydrophilic unit which contains one or more of the same or different groups selected from the group consisting of amine, amine oxide, ammonium, ammonioalkylcarboxylate, ammonioalkyl-sulphonate, amide, sulphonamide, ether, thioether, sulphoxide, hydroxyl, ester and acid group.

2. The composition of claim 1 wherein A represents a group of the formula

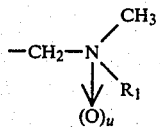 (a)

wherein $R_1$ represents $CH_3$ or $-(CH_2-CH_2-O)_n H$ wherein u is 0 or 1 and n is 1-10;

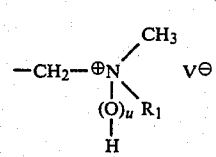 (b)

wherein $V^\ominus$ is the anion of an organic or mineral acid, $R_1$ has the meaning given in (a) above and u is 0 or 1;

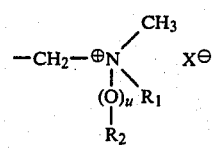 (c)

wherein $R_2$ is methyl, hydroxyethyl or dihydroxypropyl, $X^\ominus$ is an anion, and $R_1$ and u have the meanings given in (a) above;

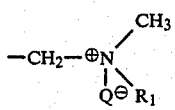 (d)

wherein $Q^\ominus$ is $-CH_2COO^\ominus$, $-CH_2-CH_2-COO^\ominus$ or $-CH_2-CH_2-CH_2-SO_3^\ominus$ and $R_1$ has the meaning given in (a) above;

$-(CH_2-S-CH_2)_w-CONH-(CH_2)_m-B$ (e)
  $\downarrow$
  $(O)_u$ wherein m is 2 or 3, u and w each independently are 0 or 1 and B is

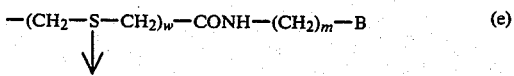

or additionally if w is 0, the group

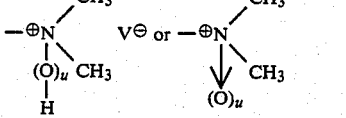

wherein u is 0 or 1, $V^\ominus$ has the meaning given in (b) above, $R_2$ and $X^\ominus$ have the meanings given in (c) above, and $Q^\ominus$ has the meaning given in (d) above;

$-CH_2-O-SO_2NH-(CH_2)_m-B$ (f)

wherein m is 2 or 3 and B has the meaning given in (e) above when w is 0;

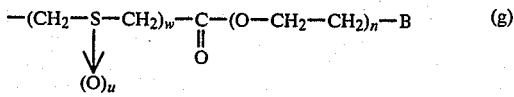 (g)

wherein n has the meaning given in (a) above, w is 0 or 1 and u and B have the meanings given in (e) above;

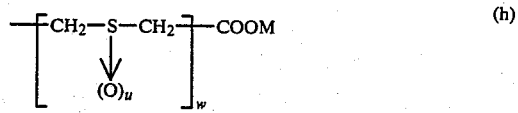 (h)

wherein M is hydrogen, ammonium or alkali metal, and u and w each independently are 0 or 1;

(i) $-CH_2-O-SO_3M$ wherein M has the meaning given in (h) above;

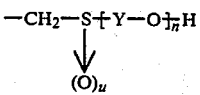 (j)

wherein Y is ethylene or hydroxypropylene, u is 0 or 1 and n is 1-10; and

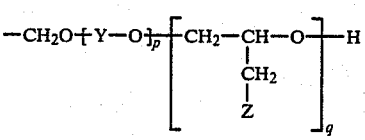 (k)

wherein p and q, each independently are 0 or a positive number up to 10, with the proviso that p and q are not 0 simultaneously, Y has the meaning given in (j) above and Z is one of $-OH$,

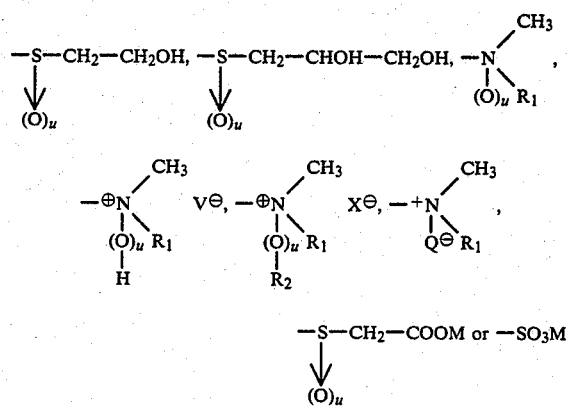

$-S-CH_2-COOM$ or $-SO_3M$, furthermore, when p is 0 or when Y is ethylene, Z can also be one of $-OSO_3M$ or $-OCO-CH_2-SO_3M$, wherein u is 0 or 1, $R_1$ has the meaning given in (a) above, $V^\ominus$ has the meaning given in (b) above, $R_2$ and $X^\ominus$ have the meanings given in (c)

above, $Q^{\ominus}$ has the meaning given in (d) above the M has the meaning given in (h) above.

3. The composition of claim 1 wherein x is an integer from 3 to 6.

4. The composition of claim 1 wherein A is —CH$_2$—N(CH$_3$)CH$_2$CH$_2$OH, —CONH(CH$_2$)$_3$N(CH$_3$)$_2$, —CH$_2$—S—CH$_2$—COOH, —CH$_2$OSO$_3$Na, $$-CH_2O(CH_2-\underset{\underset{CH_2OH}{|}}{CH}-O)_{\overline{5}}H \text{ or}$$

-continued
$$-CH_2O(CH_2-\underset{\underset{CH_2OH}{|}}{CH}-O)_{\overline{5}}(CH_2-\underset{\underset{\underset{S-CH_2-COOH}{|}}{CH_2}}{CH}-O)_{\overline{5}}H.$$

5. The composition of claim 1 wherein said hair dye is an oxidation dye precursor of the para type, optionally with one or more couplers, or a direct dyestuff selected from the group consisting of nitrobenzene dye and azo dye.

6. The composition of claim 1 wherein said polysiloxane is present in an amount of at least $0.5 \times 10^{-2}$ g/liter.

7. A process for dyeing hair comprising applying to said hair, in an amount effective to dye said hair, the composition of claim 1.

* * * * *